(12) United States Patent
Goris

(10) Patent No.: US 6,692,128 B2
(45) Date of Patent: Feb. 17, 2004

(54) OPHTHALMIC REFRACTOR HAVING GEAR PHASING HUB

(75) Inventor: Christopher Goris, Lancaster, NY (US)

(73) Assignee: Reichert, Inc., Depew, NY (US)

( * ) Notice: Subject to any disclaimer, the term of this patent is extended or adjusted under 35 U.S.C. 154(b) by 93 days.

(21) Appl. No.: 10/136,645

(22) Filed: May 1, 2002

(65) Prior Publication Data

US 2003/0206274 A1 Nov. 6, 2003

(51) Int. Cl.[7] .................................................. A61B 3/02
(52) U.S. Cl. ...................................................... 351/234
(58) Field of Search .............................. 351/200, 222, 351/227–230, 233–238, 246

(56) References Cited

U.S. PATENT DOCUMENTS

| | | | | |
|---|---|---|---|---|
| 3,860,330 A | * | 1/1975 | Persson | 351/235 |
| 4,523,822 A | * | 6/1985 | Thurston | 351/234 |
| 4,606,624 A | * | 8/1986 | Wood | 351/234 |
| 4,820,040 A | * | 4/1989 | Sims | 351/234 |
| 4,840,479 A | * | 6/1989 | Sims | 351/235 |
| 4,943,162 A | * | 7/1990 | Sims | 351/235 |
| 5,104,214 A | * | 4/1992 | Sims | 351/235 |
| 5,120,124 A | * | 6/1992 | Sims | 351/235 |
| 5,281,984 A | * | 1/1994 | Burton et al. | 351/234 |
| 5,381,196 A | * | 1/1995 | Luce et al. | 351/234 |
| 5,812,241 A | * | 9/1998 | Doms et al. | 351/235 |

* cited by examiner

Primary Examiner—George Manuel
Assistant Examiner—John R. Sanders
(74) Attorney, Agent, or Firm—Hodgson Russ LLP

(57) ABSTRACT

A subjective ophthalmic refractor comprises a cylinder power adjustment knob for simultaneously actuating a cylinder power scale and an indexable lens carrier drive assembly. The drive assembly includes a gear phasing hub designed to allow a scale marking to be centered in a display window of the refractor and components of the drive assembly to be set in proper rotational orientation as independent operations.

10 Claims, 4 Drawing Sheets

OPHTHALMIC REFRACTOR HAVING GEAR PHASING HUB

FIELD OF THE INVENTION

The present invention relates generally to ophthalmic instruments, and more particularly to subjective ophthalmic refractors for evaluating refractive characteristics of a patient's eye.

BACKGROUND OF THE INVENTION

A subjective ophthalmic refractor typically comprises left-eye and right-eye batteries each having a defined viewing path along which an operator may selectively introduce combinations of testing lenses having known refractive properties. During examination, the patient is positioned in a darkened room with his or her eyes aligned to view a projected target chart along the viewing paths defined by the left-eye and right-eye batteries. The operator then performs well-known refracting procedures, including refraction using astigmatic charts and the Jackson cross-cylinder test. A goal of the examination procedure is to determine the sphere power, cylinder power, and cylinder axis of each eye so that a suitable pair of corrective lenses may be prescribed.

U.S. Pat. No. 2,968,213 describes an ophthalmic refractor of the prior art. FIG. 5 of the '213 patent is an exploded view illustrating the internal components of a left eye lens battery, and serves to illustrate a longstanding arrangement for mechanically coupling a pair of rotatable cylinder lens carriers 8 and 9 and an associated ring-shaped cylinder power scale 50 of the battery to an adjustment knob 20 used by the operator to set a chosen cylinder power in the viewing path of the battery. As can be seen at FIG. 1 of the '213 patent, the indicia on scale 50 can be viewed by the operator through an display window or opening 52 in the battery housing. Typically, the indicia are numerical cylinder power values from 0 to 6.00 diopters in quarter-diopter increments, and are angularly spaced at regular angular increments about a central axis of the ring-shaped scale. The mechanical interconnections from knob 20, through cylinder power scale 50, to the lens carriers 8 and 9 are designed such that rotation of knob 20 positions two lenses (or a lens and an empty lens cell), one from lens carrier 8 and one from lens carrier 9, in series in the viewing path to produce a resultant cylinder power. Lens carrier 8 is a "weak" cylinder lens carrier having, for example, a blank lens cell (zero power) and four cylinder lenses ranging in power from 0.25 diopters to 1.00 diopters at quarter diopter increments. Meanwhile, lens carrier 9 is a "strong" cylinder lens carrier having, for example, a blank lens cell (zero power) and four cylinder lenses ranging in power from 1.25 diopters to 5.00 diopters at 1.25-diopter increments. Consequently, by indexing the weak cylinder lens carrier 8 five times for every one index movement of strong cylinder lens carrier 9, a cylinder power range of 0.00 diopters to 6.00 diopters at quarter-diopter increments is possible in agreement with the indicia on scale 50.

With continued reference to U.S. Pat. No. 2,968,213, it will be seen that adjustment knob 20 drives a shaft 21 having at its opposite end a dual gear comprising a small front gear 23 and a larger rear gear 25. Larger gear 25 meshes with a gear 31 which is fixedly and permanently attached to driver plate 27 in coaxial arrangement therewith, whereby rotation of knob 20 and larger gear 25 produces counter-rotation of driver plate 27. As driver plate 27 rotates about its axis, four short pegs. 39a–39d on the driver plate successively engage weak cylinder lens carrier 8 to index only the weak lens carrier, and a fifth longer peg 40 engages both the weak and strong lens carriers 8 and 9 to index both carriers, in the manner of a Geneva mechanism. A spring-biased roller 48' cooperates with five circumferential detents 53' in driver plate 27 to allow the operator to feel each index position at adjustment knob 20. A locking plate 37 having a recess 49 is fixedly mounted for rotation with driver plate 27 by a hub 33 and cooperates with a star wheel 47 on strong cylinder lens carrier 9 to prevent rotation of the strong cylinder lens carrier except when it is time for the strong cylinder lens carrier to index.

Meanwhile, small front gear 23 meshes with internal gear teeth on ring-shaped scale 50 to rotate the scale in coordination with the indexing of cylinder lens carriers 8 and 9, whereby an appropriate cylinder power value marked on the scale appears through display window 52. Scale 50 is constrained both radially and axially by three bearings 56 located at respective positions about the circumference of scale 50.

During manufacturing assembly of an ophthalmic refractor formed in accordance with the '213 patent, it is necessary to carefully align cylinder power scale 50 such that a correct cylinder power value is precisely centered in display window 52 while dependent rotational positions of driver plate 27 and locking plate 37 are also in proper alignment for functioning of the Geneva mechanism. However, because an exact locational relationship between the internal gear teeth and the markings on scale 50 is not specified and one scale differs slightly from another in this regard, the task of centering the scale markings in the display window and achieving proper rotational alignment among the interconnected parts has involved a process of trial and error. For example, different scales 50 and other component parts in the mechanical interconnection are tried from production batches of these parts until a suitable combination of parts produces acceptable rotational alignment and centering of the scale markings.

FIGS. 2 and 3 herein help illustrate assembly of an ophthalmic refractor eye battery 111A according to the prior art. A cylinder power scale 118 is mounted in eye battery housing 112A, and adjustment knob shaft 124 is inserted through a provided bearing opening in the housing such that scale drive gear 126 (see small front gear 23 of the '213 patent) fixed to the shaft meshes with internal gear 130 of cylinder power scale 118. A driver plate 127 having a gear 131 permanently fixed thereto and a locking plate 133 having a hub 135 permanently fixed thereto are fastened together in a predefined angular relationship such that an arcuate recess 159 of the locking plate is centered with respect to the longer peg 160 of the driver plate. More specifically, three angularly spaced fastener holes 145 are provided through hub 135 in set relation to recess 159 and three corresponding threaded holes 147 are provided through gear 131 in set relation to longer peg 160, and the hub 135 is fastened to gear 131 by threaded fasteners 149 operable through access openings 151 to form a subassembly 153 comprising locking plate 133, hub 135, driver plate 127, and gear 131. This subassembly 153 is then mounted on hub stem 137 such that gear 131 meshes with a larger gear 128 (see larger rear gear 25 of the '213 patent) fixed to adjustment knob shaft 124 adjacent scale drive gear 126. A spring-biased roller (not shown in FIGS. 2 and 3 but equivalent to spring-biased roller 48' shown in the '213 patent) engages an appropriate detent 155 in driver plate 127 to set the relationship of subassembly 153 to a star wheel and lens carriers (not shown in FIGS. 2 and 3 but equivalent to star wheel 47 and lens carriers 8 and 9 of the '213 patent). Consequently, in order for gear 131 of subassembly 153 to mesh with larger gear 128, the adjustment knob shaft may have to rotate slightly, thereby rotating the scale drive gear 126 and scale 118 and producing an "uncentered" appearance of the corresponding scale marking in display window 122. To correct this, different scales 118, driver plates 127 with attached gear 131, and locking plates 133 with attached hub 135 must be tried until a satisfactory centering is achieved.

Understandably, this assembly process is time consuming and requires skill and patience on the part of the assembly technician. The introduction of tighter tolerances for the component parts can alleviate the problem to some extent, however this introduces increased costs associated with manufacturing the component parts.

SUMMARY OF THE INVENTION

Therefore, it is an object of the present invention to increase efficiency in the assembly process for manufacturing subjective ophthalmic refractors.

It is another object of the present invention to improve the precision with which cylinder power scale markings are centered in a display window of a subjective ophthalmic refractor for higher quality from one refractor to the next.

It is another object of the present invention to diminish the level of skill and patience required of an assembly technician in assembling a subjective ophthalmic refractor.

It is a further object of the present invention to achieve the objects stated above without introducing more exacting tolerances with respect to component parts of the ophthalmic refractor.

In furtherance of these and other objects, an ophthalmic refractor of a type comprising a cylinder power adjustment knob operatively connected to a drive assembly for indexing at least one rotatable lens carrier and to a corresponding rotatable cylinder power scale is made easier to assemble at a higher level of quality with respect to centering of scale markings in a display window. More specifically, the drive assembly can be set in a required rotational orientation separately from and after the centering of an appropriate scale marking in a display widow of the eye battery housing without affecting the centered position of the scale marking. In accordance with a preferred embodiment, the cylinder power adjustment knob is coupled to a shaft that carries a pair of gears at its distal end for rotation with the adjustment knob, a first gear for transmitting torque to the cylinder power scale and a second gear for transferring torque to a Geneva mechanism drive assembly and the other gear. The second gear meshes with a third gear that is coaxial with a driver plate of the Geneva mechanism. A gear phasing hub is adjustable axially relative to the third gear to selectively clamp the driver plate to the third gear at any necessary rotational orientation. An end cap threadably received by the gear phasing hub secures a locking plate of the Geneva mechanism to the, gear phasing hub in a proper rotational orientation relative to the driver plate. Thus, both the driver plate and locking plate can be set without disturbing the centered condition of the cylinder power scale.

BRIEF DESCRIPTION OF THE DRAWING

The nature and mode of operation of the present invention will now be more fully described in the following detailed description of the invention taken with the accompanying drawing figures, in which.

DETAILED DESCRIPTION OF THE INVENTION

Figure 1:
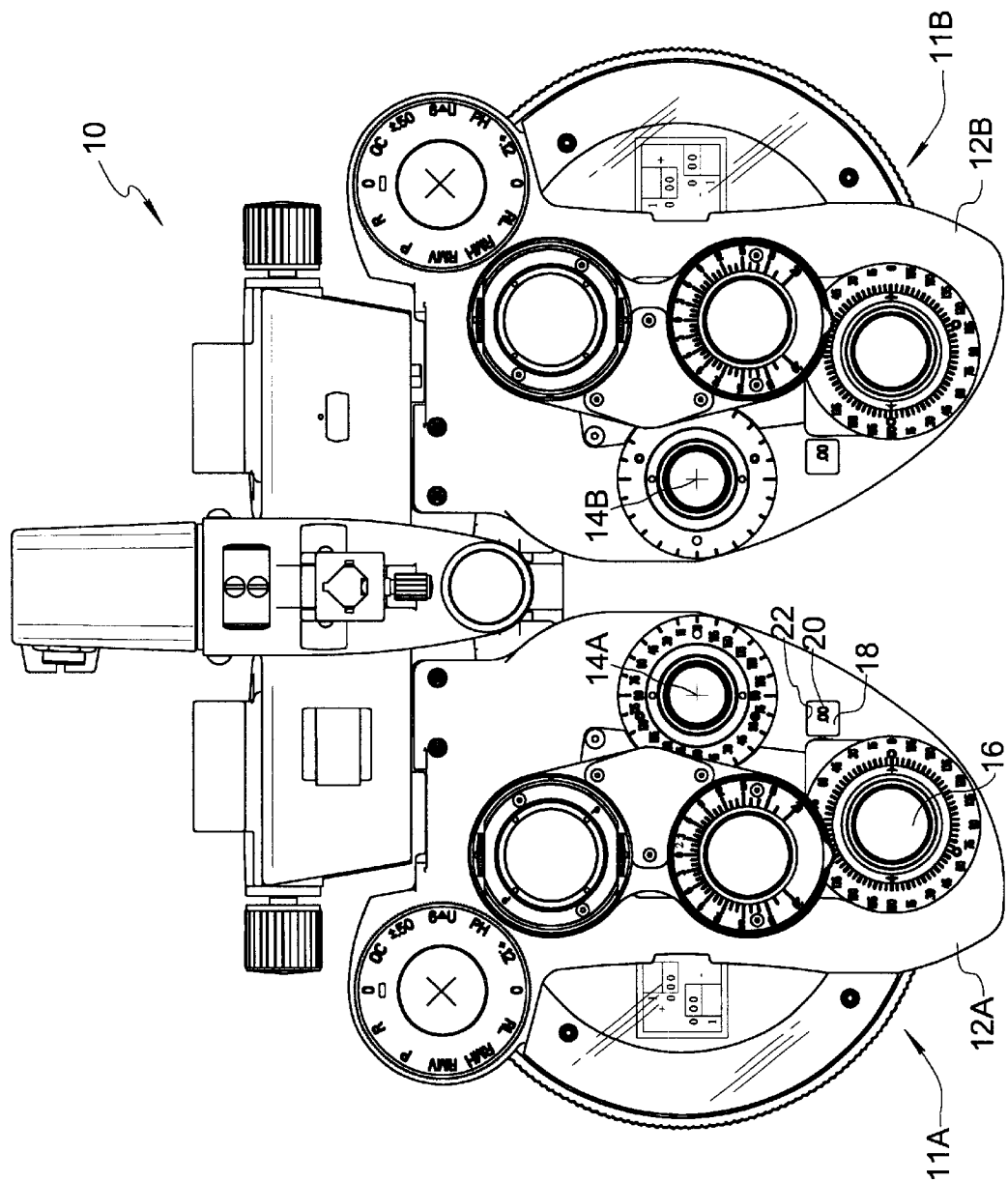
FIG. 1 is a front elevational view of an ophthalmic refractor formed in accordance with a preferred embodiment of the present invention.
Figure 2:
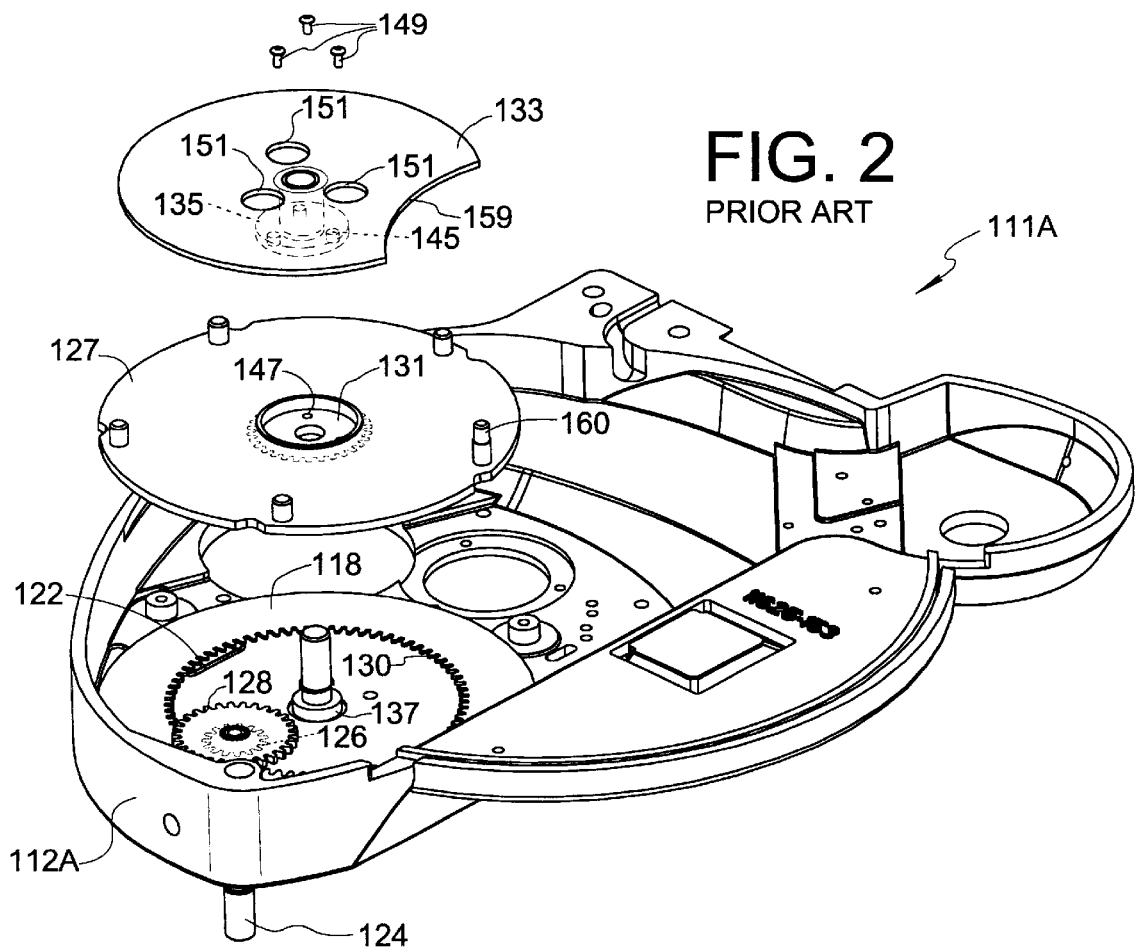
FIG. 2 is an exploded perspective view of an eye battery of an ophthalmic refractor illustrating a construction according to the prior art.
Figure 3:
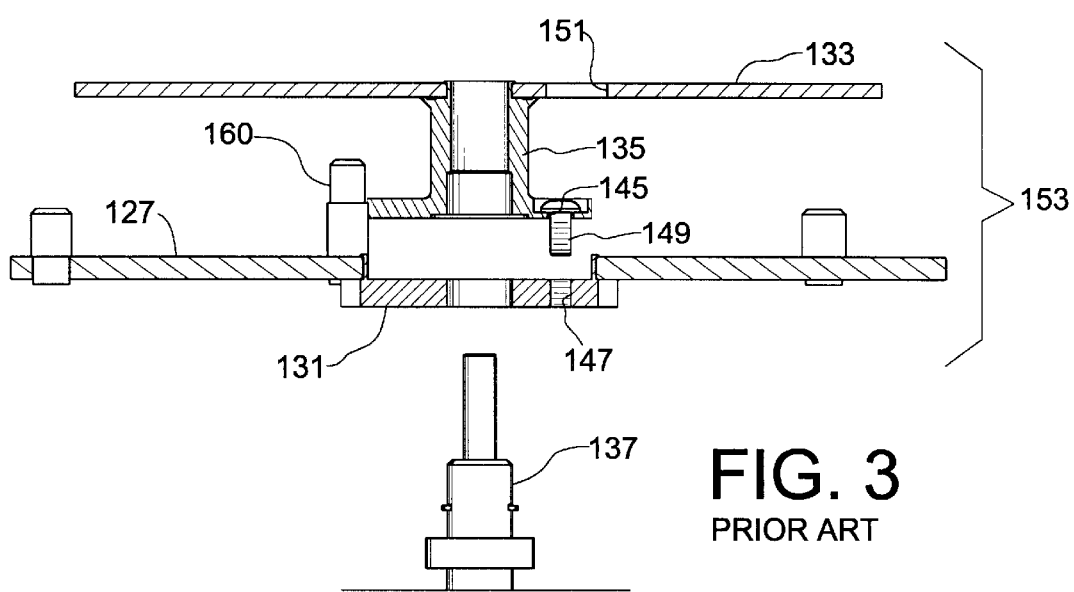
FIG. 3 is a cross-sectional view illustrating the assembly of a driver plate and a locking plate of the prior art eye battery shown in FIG. 2.

FIG. 1 shows a subjective ophthalmic refractor 10 formed in accordance with a preferred embodiment of the present invention. Ophthalmic refractor 10 is of a type well-known in the art of ophthalmic instruments in that it generally comprises a right eye battery 11A and a left eye battery 11B that are mirror images of each other. Eye batteries 11A and 11B comprise respective housings 12A and 12B and respective viewing paths 14A and 14B along which a patient facing a back side of the instrument gazes during examination. The construction and operation of ophthalmic refractor 10 are generally and substantially as taught in U.S. Pat. Nos. 2,968,213 and 2,995,065, both these patents being incorporated herein by reference.

Figure 6:
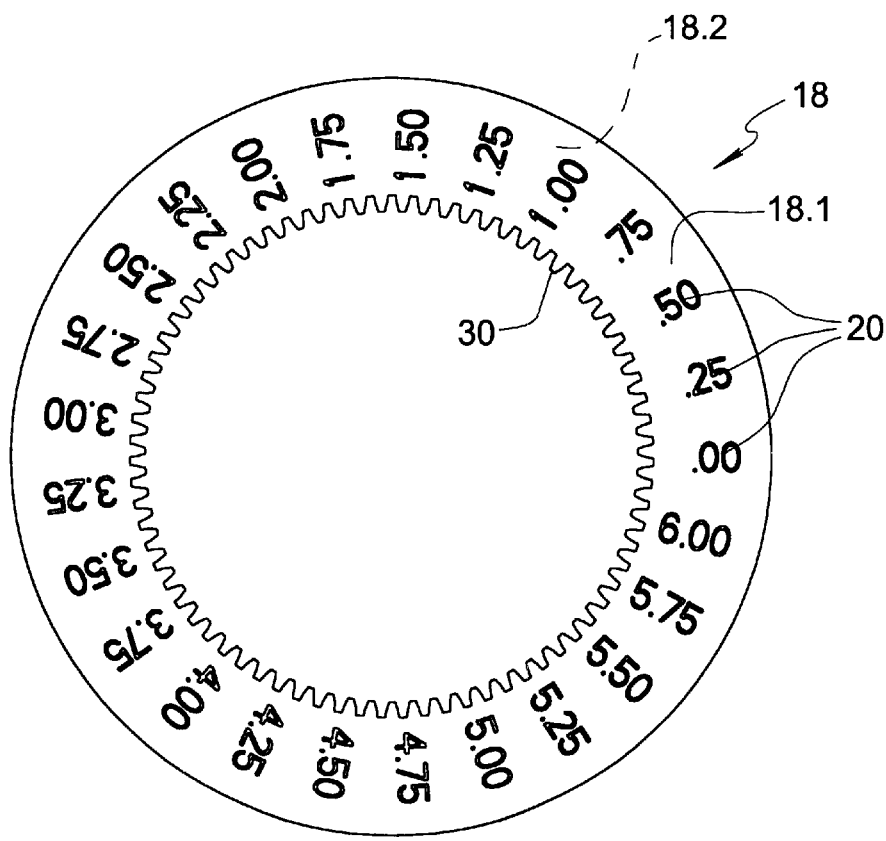
FIG. 6 is a plan view of a cylinder power scale of the eye battery shown in FIG. 4.

The present invention relates to an improvement involving a cylinder power adjustment system found in each eye battery 11A and 11B. For sake of simplicity, the invention is described with respect to right eye battery 11A only, it being understood that left eye battery 11B is a mirror image of right eye battery 11A. Battery 11A comprises a cylinder power adjustment knob 16, a cylinder power scale 18 having numerical markings 20 indicative of a cylinder power introduced in viewing path 14A (see FIG. 6), and an opening or display window 22 in battery housing 12A for allowing an appropriate power value on scale 18 to be viewed by an ophthalmic practitioner.

Figure 4:
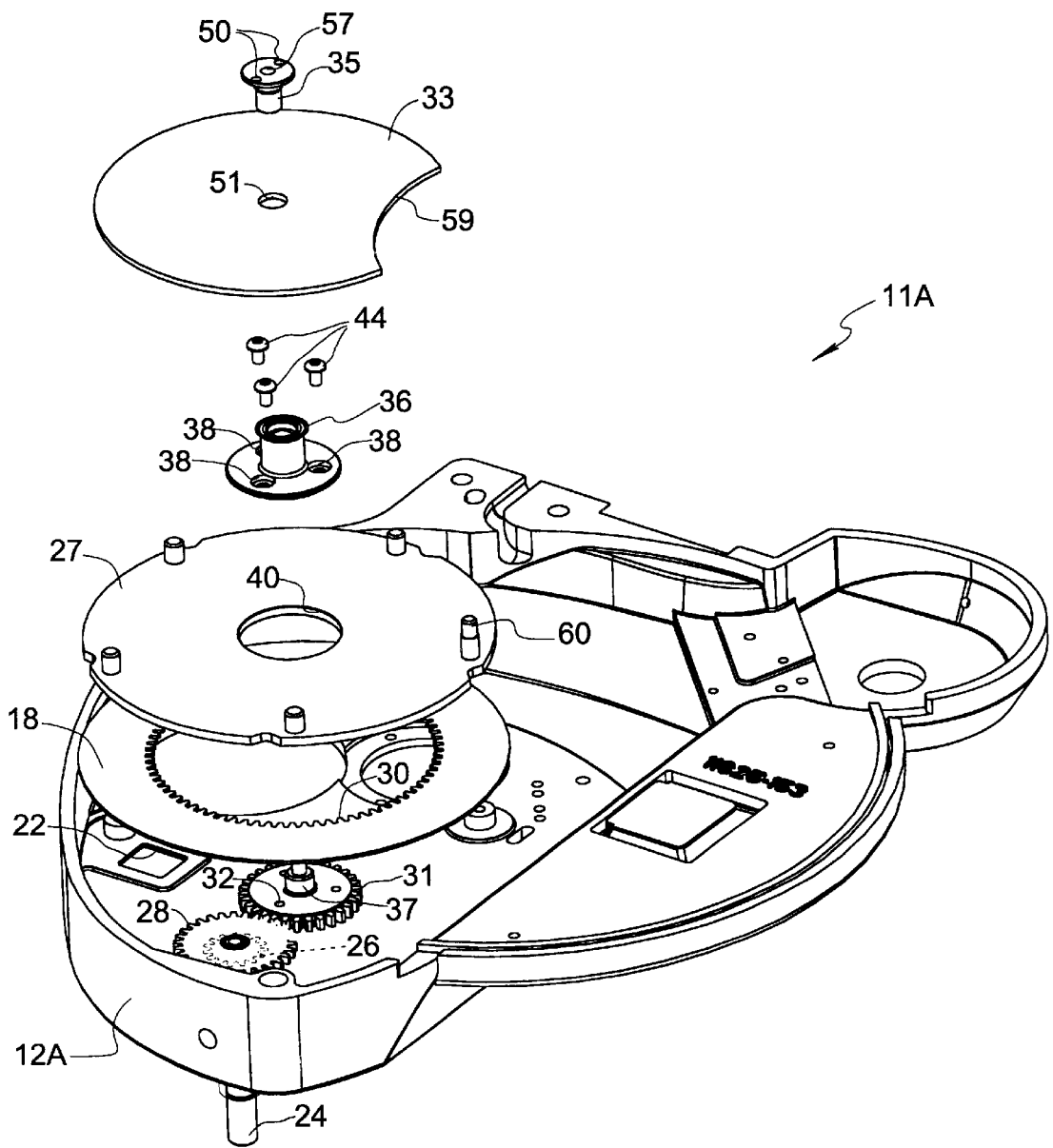
FIG. 4 is an exploded perspective view of an eye battery of the ophthalmic refractor shown in FIG. 1 and incorporating the present invention.
Figure 5:
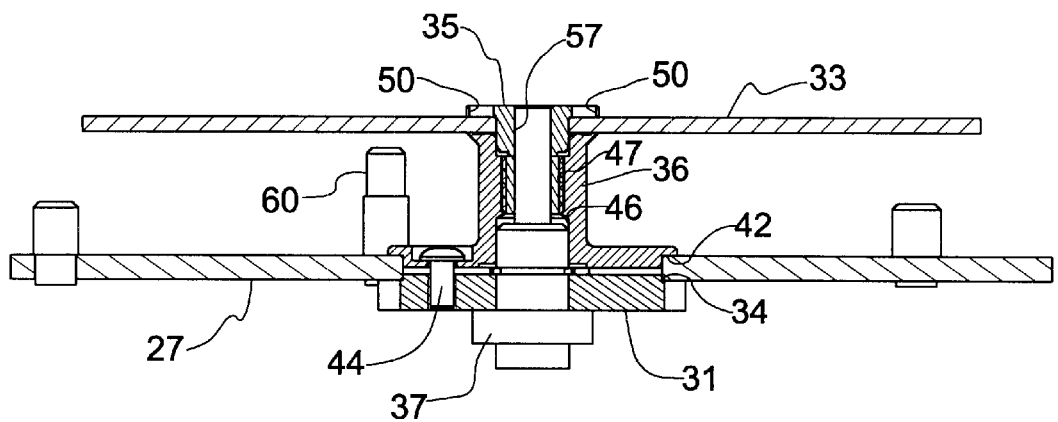
FIG. 5 is a cross-sectional view showing assembly of a driver plate and a locking plate of the eye battery shown in FIG. 4 in accordance with the present invention.

Referring also now to FIGS. 4 and 5 of the drawings, adjustment knob 16 is fixed on a shaft 24 having at its opposite end a dual gear comprising a small front gear 26 and a larger rear gear 28. Larger gear 28 transmits torque to a Geneva mechanism for indexing a pair of cylinder lens carriers (not shown) as described in referenced U.S. Pat. No. 2,968,213. In the relevant portion shown in FIG. 4, the Geneva mechanism includes a gear 31, a driver plate 27, a gear phasing hub 36, a locking plate 33, and an end cap 35 aligned coaxially on an axle stem 37 fixed to eye battery housing 12A.

Larger rear gear 28 on adjustment knob 24 meshes with gear 31, which is rotatably mounted on an axle stem 37 and has a plurality of threaded fastener holes 32 spaced about its rotational axis. Gear 31 includes a radial step 34 defining a radially reduced portion received in close slidable fit within a circular opening 40 through driver plate 27 centered on a common rotational axis of gear 31 and the driver plate. Likewise, gear phasing hub 36 has a plurality of fastener holes 38 corresponding to threaded holes 32 in gear 31, and includes a radial step 42 defining a radially reduced portion received in close slidable fit within circular opening 40. Accordingly, as best seen in FIG. 5, a plurality of threaded fasteners 44 extend through fastener holes 38 in gear phasing hub 36 and mate with threaded holes 32 in gear 31, whereby gear phasing hub 36 can be adjusted axially relative to gear 31. When fasteners 44 are tightened, gear phasing hub 36 securely clamps driver plate 27 to gear 31. However, when fasteners 44 are loosened, driver plate 27 can be rotated independently of gear 31 and vice versa. Consequently, an assembly technician can selectively secure driver plate 27 to gear 31 at any chosen angular orientation relative to gear 31.

Gear phasing hub 36 is provided with a radially stepped axial opening 46 slidably fitting over axle stem 37 as shown in FIG. 5. Axial opening 46 includes an internally threaded portion 47 into which a threaded shank 48 of end cap 35 is mated after the shank passes through a central aperture 51 in locking plate 33. When end cap 35 is tightened, it serves to securely clamp locking plate 33 to gear phasing hub 36. When end cap 35 is loosened, locking plate 33 and gear phasing hub 36 are rotationally independent of one another. Therefore, an assembly technician can selectively secure locking plate 33 to gear phasing hub 36 at any chosen angular orientation relative to gear phasing hub 36. In the preferred embodiment shown herein, end cap 35 includes a pair of spaced holes 50 for receiving corresponding prongs of a specially made adjustment tool (not shown) for tightening and loosening the end cap. End cap 35 is further provided with a central axial passage 57 sized for slidable fit onto axle stem 37.

Small gear 26 on adjustment knob shaft 24 meshes with an internal gear 30 of cylinder power scale 18 to rotate the cylinder power scale simultaneously and in concert with the rotational indexing of the cylinder lens carriers via the Geneva mechanism. Cylinder power scale 18 includes a frontward-facing first side 18.1 on which markings 20 are applied, and a rearward-facing second side 18.2.

As will be understood from the foregoing description, it is now possible during assembly of eye battery 11A to adjust scale 18 independently of driver plate 27 until an appropriate scale marking is centered with respect to display window 22, and then subsequently secure the driver plate 27 to gear 31 by means of gear phasing hub 36 and fasteners 44 such that driver plate 27 is at its proper rotational orientation. Moreover, the rotational orientation of locking plate 33 relative to driver plate 27 can be selectively adjusted and set by means of end cap 35 such that an arcuate recess 59 of locking plate 33 is centered with respect to a long peg 60 of driver plate 27. As a consequence of the present invention, scale markings 20 are centered to a high degree within display window 22 in a fraction of the assembly time required for ophthalmic refractors of the prior art.

What is claimed is:

1. An ophthalmic refractor comprising:
a viewing path;
a housing having a display window;
a lens carrier holding a plurality of lenses, said lens carrier being rotatably mounted in said housing to permit a chosen one of said plurality of lenses to be positioned in said viewing path;
a rotatable adjustment knob;
first and second gears fixed to said adjustment knob for rotation therewith;
a ring-shaped scale including an internal gear meshing with said first gear, said scale having angularly spaced markings viewable through said display window;
a third gear meshing with said second gear;
a driver plate coaxial with said third gear and operatively connected to said lens carrier for rotating said lens carrier; and
means for selectively securing said driver plate to said third gear at any chosen angular orientation relative to said third gear.

2. The ophthalmic refractor according to claim 1, wherein said means for selectively securing said driver plate to said third gear comprises a hub adjustable in an axial direction relative to said third gear for clamping said driver plate to said third gear.

3. The ophthalmic refractor according to claim 2, wherein said hub is adjustable in an axial direction relative to said third gear by operation of a plurality of threaded fasteners acting between said hub and said third gear.

4. The ophthalmic refractor according to claim 3, wherein said driver plate includes an opening therethrough, and said plurality of threaded fasteners extend through said opening.

5. The ophthalmic refractor according to claim 4, wherein said opening through said driver plate is a circular opening centered on a rotational axis of said third gear and said driver plate, and said hub and said third gear each include a radial step such that a portion of said hub and a portion of said third gear extend axially into said opening in close slidable fit with an internal wall of said opening.

6. The ophthalmic refractor according to claim 2, wherein said hub comprises an axially extending threaded hole and said ophthalmic refractor further comprises an end cap having a threaded shank for mating with said threaded hole of said hub, whereby an additional element can be releasably secured to said hub for rotation therewith.

7. An ophthalmic refractor comprising:
a viewing path;
a housing having a display window;
at least one lens carrier holding a plurality of lenses, said at least one lens carrier being mounted in said housing for rotation about a carrier axis to permit a chosen one of said plurality of lenses to be positioned in said viewing path;
a rotatable adjustment knob;
a drive assembly operably connected to said adjustment knob for rotating said at least one lens carrier in response to rotation of said adjustment knob;
a rotatable scale operably connected to said adjustment knob, said scale having angularly spaced markings viewable through said display window and said scale rotating in response to rotation of said adjustment knob; and
means for temporarily disconnecting said drive assembly from said adjustment knob to allow independent rotation, of said scale in response to rotation of said adjustment knob without an accompanying actuation of said drive assembly.

8. The ophthalmic refractor according to claim 7, wherein said at least one lens carrier includes:
a weak lens carrier holding a plurality of weak power lenses, said weak lens carrier being mounted in said housing for rotation about said carrier axis to permit a chosen one of said plurality of weak power lenses to be positioned in said viewing path; and
a strong lens carrier holding a plurality of strong power lenses, said strong lens carrier being mounted in said housing for rotation about said carrier axis to permit a, chosen one of said plurality of strong power lenses to be positioned in said viewing path.

9. The ophthalmic refractor according to claim 7, wherein said drive assembly includes a Geneva mechanism.

10. The ophthalmic refractor according to claim 9, wherein said Geneva mechanism includes a gear driven in response to rotation of said adjustment knob; a hub adjustably fastened to said gear; a driver plate having a plurality of driver pegs for engaging said at least one lens carrier, said driver plate being releasably clamped between said gear and said hub; a locking plate; and an end cap adjustably mating with said hub for releasably securing said locking plate to said hub.

* * * * *